United States Patent [19]

Goldberg et al.

[11] 4,219,568

[45] Aug. 26, 1980

[54] METHOD OF INCREASING RENAL BLOOD FLOW WITH DOPAMINE DERIVATIVES

[75] Inventors: Leon I. Goldberg, Chicago, Ill.; Joseph G. Cannon; John P. Long, both of Iowa City, Iowa

[73] Assignee: University Patents, Inc., Norwalk, Conn.

[21] Appl. No.: 882,353

[22] Filed: Mar. 1, 1978

[51] Int. Cl.² .......................................... A61K 31/135
[52] U.S. Cl. .................................... 424/330; 424/316
[58] Field of Search ................................ 424/330, 316

[56] References Cited

U.S. PATENT DOCUMENTS 4,014,937  3/1977  Richardson ........................... 424/330

OTHER PUBLICATIONS

Volkman et al., Fed. Proc., vol. 36, No. 3, Mar. 1, 1977, Ab. No. 4093, p. 1049.
Ginos et al., Fed. Proc., vol. 37, No. 3, Mar. 1, 1978, Ab. No. 2482, p. 683.

*Primary Examiner*—Anna P. Fagelson
*Attorney, Agent, or Firm*—Mathew L. Kalinowski

[57] ABSTRACT

Certain N,N-dialkyl substituted derivatives of dopamine (DA) increase renal blood flow without affecting cardiac contractility. Particularly effective are N,N-di-n-propyl DA; N-n-propyl-N-n-butyl DA; N-n-propyl-N-n-pentyl DA; N-n-propyl-N-isobutyl DA; and N-n-propyl-N-phenethyl DA. Orally effective versions of these derivatives are obtained by acylating the hydroxyl functions.

9 Claims, 1 Drawing Figure

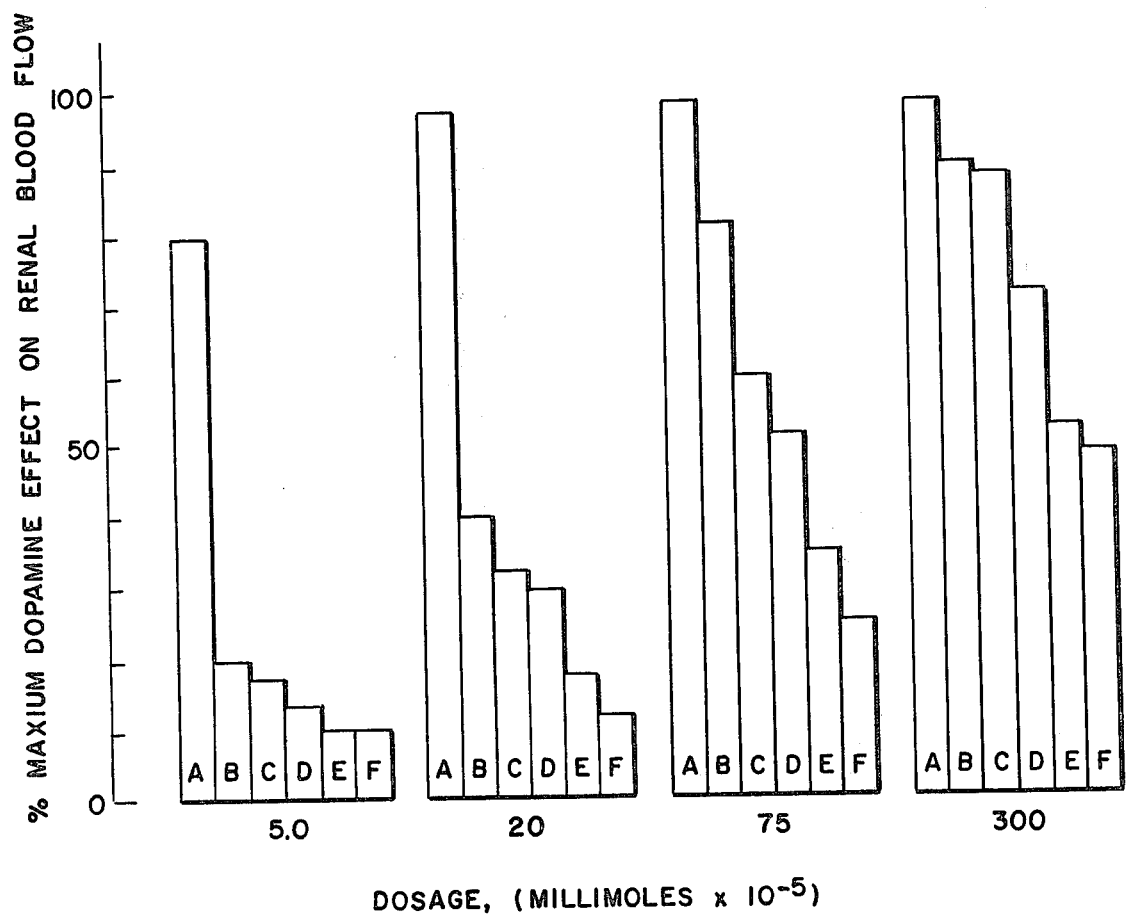

METHOD OF INCREASING RENAL BLOOD FLOW WITH DOPAMINE DERIVATIVES

BACKGROUND OF THE INVENTION

The invention described herein was made in the course of work under a grant from the Department of Health, Education and Welfare.

This invention relates to a method for increasing renal blood flow without affecting cardiac contractility. More particularly, this invention relates to increasing renal blood flow without affecting cardiac contractility by administering suitable dosages of certain N,N-dialkyl substituted derivatives of dopamine.

Dopamine (3,4-dihydroxyphenylethylamine) has the ability to dilate renal mesenteric and other blood vessels by acting on specific dopamine receptors. Because of this action dopamine is useful in the treatment of shock and congestive heart failure. The basic aspects relating to the activity of dopamine are well known and are reviewed by L. I. Goldberg, *Pharmacol. Rev.*, 24:19, 1972; clinical uses are described by L. I. Goldberg, *New Eng. J. Med.*, 291:707, 1974. Both of these citations are incorporated herein by references as illustrative of the state of the art.

Although dopamine is effective in increasing renal blood flow, it may be contra-indicated in certain patients because it stimulates the heart by acting on $\beta$-adrenergic receptors and by releasing norepinephrine from myocardial storage sites.

Therefore, it is an object of this invention to provide a method of increasing renal blood flow without at the same time stimulating cardiac activity. It is a further object of this invention to increase renal blood flow without stimulating cardiac activity by administering certain N,N-dialkyl substituted derivatives of dopamine. These and other objects will become apparent as the description of the invention proceeds.

BRIEF SUMMARY OF THE INVENTION

In accordance with the instant invention, dopamine-like activity without cardiac stimulation is provided by compounds having the formula:

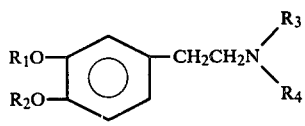

where $R_1$ and $R_2$ are hydrogen or an acyl group containing from 2 to about 6 carbon atoms; $R_3$ is a n-propyl substituent; and $R_4$ is a n-propyl, n-butyl, isobutyl, n-pentyl, or a phenethyl substituent. Particularly suitable material for parenteral administration is provided when $R_1$ and $R_2$ are hydrogen. Oral administration can be employed to advantage when $R_1$ and $R_2$ are acyl groups having from 2 to about 6 carbon atoms, for example acetyl or 2,2-dimethylpropacyl substituents.

The above-identified compounds of this invention are prepared by methods known in the art, for example by the sequence of reactions taught by Ginos, et al *J. Med. Chem.* 18, No. 12, p. 1197 (1975), which teaching is incorporated herein by reference. The preparative reaction sequence is as follows:

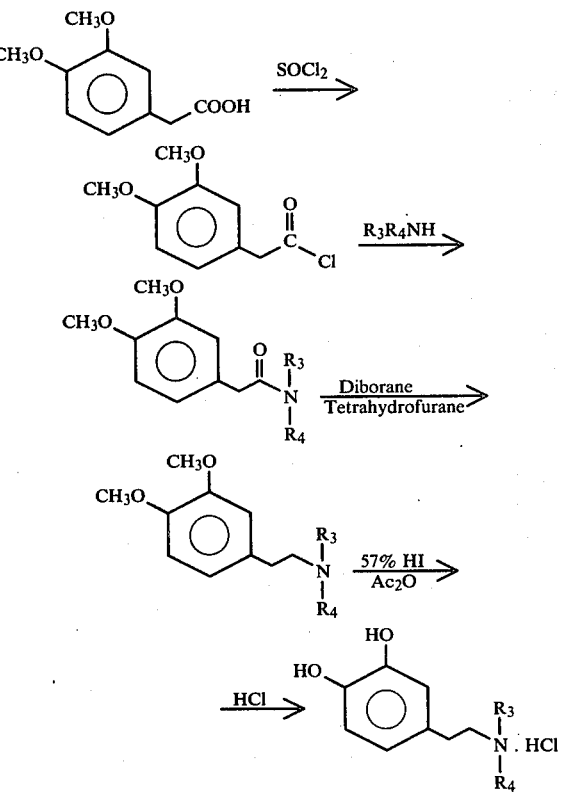

where $R_3$ and $R_4$ are the hydrocarbon groups defined in the preceding paragraph. The amine hydrochloride product is converted to the free amine by treatment with a basic reagent, suitably $NaHCO_3$.

Materials particularly suitable for oral administration are obtained by acylating one or both of the hydroxyl functions of the products of the above reaction by methods known in the art; for example, by treatment with an acyl chloride having from 2 to about 6 carbon atoms, preferrably with 2,2-dimethylpropacyl chloride.

DESCRIPTION OF THE PREFERRED EMBODIMENT

The dopamine-like activity of the inventive compounds was demonstrated in dogs anesthetized with pentobarbital, 30 mg/kg. The renal artery was exposed and an electromagnetic flow meter was attached to the artery. Intra-arterial injections were given through a 3-way stopcock connected to an infusion pump and a 25 gauge needle bent about 5 mm from the tip at a 90° angle and placed and retained in the artery by the flow from the pump. Phenoxybenzamine, 5 mg/kg, was infused over a period of 20 minutes, following which the dopamine derivative under study was injected intra-arterially to determine its effect on renal blood flow.

An additional series of experiments was conducted to determine the effects of the dopamine derivative on cardiac contractility. For this purpose, a Walton-Brodie strain gauge arch was sutured to the right ventricle of the anesthetized dog and the dopamine derivative under study was administered.

The results of these experiments are listed in Table I.

TABLE I

| Compound* | $R_3$ | $R_4$ | Activity Dopamine-like | Activity $\beta$-adrenergic |
|---|---|---|---|---|
| Dopamine (DA) | H | H | + | + |
| N-isobutyl DA | H | iso-$C_4$ | − | − |
| N-n-pentyl DA | H | n-$C_5$ | − | + |
| N-phenethyl DA | H | $C_6H_5CH_2CH_2$— | − | − |
| N-methyl-N-isobutyl DA | $CH_3$ | iso-$C_4$ | − | − |
| N-methyl-N-n-pentyl DA | $CH_3$ | n-$C_5$ | − | − |
| N-methyl-N-phenethyl DA | $CH_3$ | $C_6H_5CH_2CH_2$— | − | − |
| N,N-diethyl DA | $C_2H_5$ | $C_2H_5$ | − | − |
| N,N-di-n-propyl DA | n-$C_3$ | n-$C_3$ | + | − |
| N-n-propyl-N-n-butyl DA | n-$C_3$ | n-$C_4$ | + | − |
| N-n-propyl-N-sec-butyl DA | n-$C_3$ | sec-$C_4$ | − | − |
| N-n-propyl-N-isobutyl DA | n-$C_3$ | iso-$C_4$ | + | − |
| N-n-propyl-N-n-pentyl DA | n-$C_3$ | n-$C_5$ | + | − |
| N-n-propyl-N-phenethyl DA | n-$C_3$ | $C_6H_5CH_2CH_2$— | + | − |
| N,N-di-sec-butyl DA | sec-$C_4$ | sec-$C_4$ | − | − |
| N,N-di-isobutyl DA | iso-$C_4$ | iso-$C_4$ | − | − |
| N,N-di-n-pentyl DA | n-$C_5$ | n-$C_5$ | − | − |

:In all compounds listed, $R_1$ and $R_2$ are hydrogen in the formula

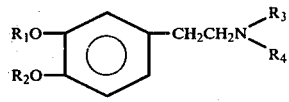

The dose response curves for the derivatives exhibiting dopamine-like activity without heart stimulation ($\beta$-adrenergic activity) are shown in FIG. 1. All of these derivatives increased renal blood flow in a qualitatively similar manner. However, the doses of N,N-di-n-propyl DA; N-n-propyl-N-n-butyl DA; and N-n-propyl-N-n-pentyl were approximately 16–30 times greater to produce the same effect as dopamine; N-n-propyl-N-isobutyl DA and N-n-propyl-N-phenethyl DA required about 100 times the dopamine dosage to produce the same effect.

In the studies on cardiac contractility, dopamine has positive, dose-related effect beginning at 4–8 μg/kg. In contrast, the dopamine derivatives exhibiting dopamine-like activity with respect to renal blood flow had no effect on cardiac contractility in doses in excess of 250 82 g/kg.

In additional experiments, it was demonstrated that the renal vasodilation produced by dopamine and the dopamine derivatives in FIG. 1 was specifically attenuated by the dopamine receptor antagonist, haloperidol. It is concluded therefore that these dopamine derivatives, like dopamine itself, increased renal blood flow by acting on dopamine vascular receptors.

Although this invention has been disclosed in detail with particular reference to certain preferred embodiments thereof, it is understood that variations and modifications can be effected within the spirit and scope of the appended claims. It is intended that all material contained in the above description, tables, and figures shall be interpreted in an illustrative and not in a limiting sense.

What is claimed is:

1. A method of increasing renal blood flow without affecting cardiac contractility comprising the step of administering to a patient in need of same an effective dose therefor of a compound having the general formula

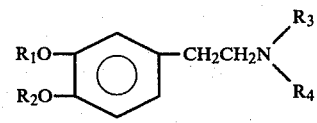

where $R_1$ and $R_2$ are hydrogen or an acyl group containing from 2 to about 6 carbon atoms, $R_3$ is a n-propyl substituent, and $R_4$ is a member selected from the group consisting of n-propyl, n-butyl, isobutyl, n-pentyl and phenethyl substituents.

2. The method of claim 1 where $R_1$ and $R_2$ are hydrogen and the compound is administered parenterally.

3. A method of claim 2 wherein $R_3$ and $R_4$ are n-propyl substituents.

4. The method of claim 2 wherein $R_3$ is n-propyl and $R_4$ is an n-butyl substituent.

5. The method of claim 2 wherein $R_3$ is n-propyl and $R_4$ is an isobutyl substituent.

6. The method of claim 2 wherein $R_3$ is n-propyl and $R_4$ is an n-pentyl substituent.

7. The method of claim 2 wherein $R_3$ is n-propyl and $R_4$ is a phenethyl substituent.

8. The method of claim 1 wherein $R_1$ and $R_2$ are acyl groups containing from 2 to about 6 carbon atoms and the compound is administered orally.

9. The method of claim 8 wherein $R_1$ and $R_2$ are 2,2-dimethylpropacyl substituents.

* * * * *